United States Patent
Bornemann

(10) Patent No.: US 6,282,944 B1
(45) Date of Patent: Sep. 4, 2001

(54) APPARATUS AND PROCESS FOR THE ANALYSIS OF EXHAUST GAS COMPONENTS

(75) Inventor: Torsten Bornemann, Monchengladbach (DE)

(73) Assignee: Pierburg AG, Neuss (DE)

( * ) Notice: Subject to any disclaimer, the term of this patent is extended or adjusted under 35 U.S.C. 154(b) by 0 days.

(21) Appl. No.: 09/464,839

(22) Filed: Dec. 16, 1999

(30) Foreign Application Priority Data

Dec. 16, 1998 (DE) ............................... 198 57 995

(51) Int. Cl.[7] ............... G01N 1/22; G01N 35/10; G01N 1/10; G01M 15/00
(52) U.S. Cl. .................. 73/23.2; 73/23.31; 73/118.1
(58) Field of Search .................. 73/23.2, 23.31, 73/23.3, 23.32, 118.1

(56) References Cited

U.S. PATENT DOCUMENTS

| | | | |
|---|---|---|---|
| 1,686,051 | * 10/1928 | Weber | 73/23.31 |
| 2,077,538 | * 4/1937 | Wait | 73/51 |
| 3,603,155 | * 9/1971 | Morris et al. | 73/421.5 R |
| 4,150,670 | * 4/1979 | Jewett et al. | 128/188 |
| 4,170,892 | * 10/1979 | Bailitis | 73/23 |
| 5,369,976 | * 12/1994 | Ratton | 73/23.2 |
| 5,526,675 | * 6/1996 | Ratton | 73/23.2 |
| 5,756,360 | * 5/1998 | Harvey et al. | 436/179 |
| 5,780,717 | * 7/1998 | Wise et al. | 73/23.2 |
| 5,846,831 | * 12/1998 | Silvis | 436/55 |
| 6,112,575 | * 9/2000 | Cocconi | 73/23.31 |
| 6,138,499 | * 10/2000 | Hoede et al. | 73/23.31 |

* cited by examiner

*Primary Examiner*—Hezron Williams
*Assistant Examiner*—David J. Wiggins
(74) *Attorney, Agent, or Firm*—Ladas & Parry

(57) ABSTRACT

Apparatus and process for the analysis of exhaust gas components in which the exhaust gas from an internal combustion engine is supplied to a sample gas line connected to at least one sample bag connected to a gas composition analyzer. The sample bag is contained in a gas-tight and pressure-resistant container, which is connected to a vacuum source to maintain a specified vacuum in the container thereby to apply the vacuum to the sample bag during the time interval in which exhaust gas measurements are being conducted.

3 Claims, 1 Drawing Sheet

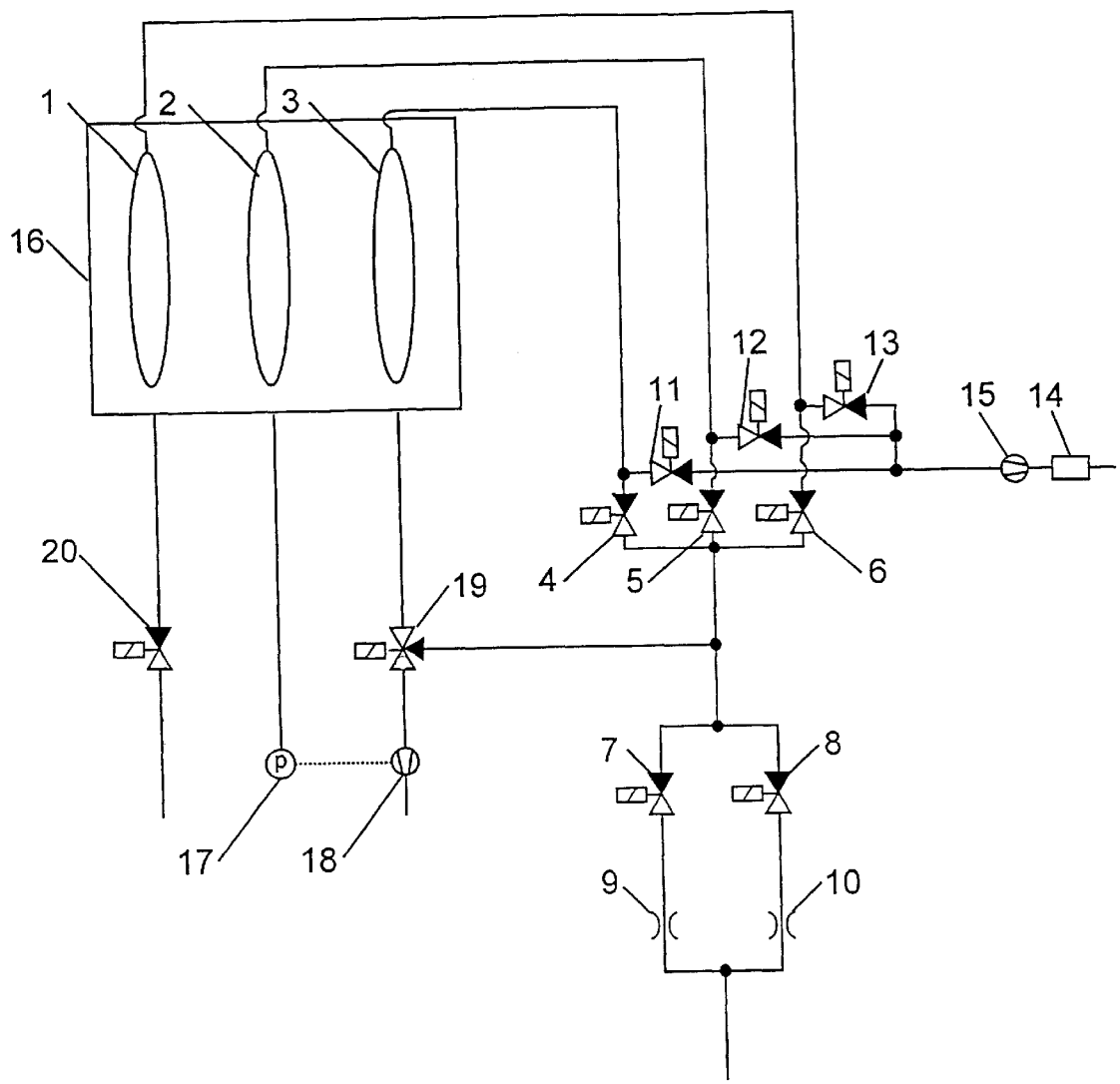

APPARATUS AND PROCESS FOR THE ANALYSIS OF EXHAUST GAS COMPONENTS

FIELD OF THE INVENTION

The invention relates to an apparatus and a process for the analysis of exhaust gas components from an internal combustion engine.

BACKGROUND

Apparatus and processes for the measurement of exhaust gas components of internal combustion engines have been known for a long time. In the so-called CVS (Constant Volume Sampling) process, the exhaust gas produced during a test is introduced into the intake flow of a constantly transporting conveyor. The conveyor has a transport capacity, which lies clearly above the maximum exhaust gas volume flow of the vehicle engine under full load. The volume difference that occurs between the exhaust gas quantity and the conveyor capacity is equilibrated by intake of filtered fresh air that fulfills the dual functions of providing exhaust gas dilution and constant gas/air volume flow rate. Samples are taken and collected in sample bags from the exhaust gas air mixture during the entire test with uniform volume flow. The concentrations of pollutants and carbon dioxide are measured in the samples prepared in this way. However, a problem arises in that the emissions of modern engines and vehicles are becoming increasingly smaller. The measured concentrations often approach the detection limits of the analytical technique, so that the results of analysis are unreliable. One remedy is to make the dilution ratio smaller and thus the concentration of exhaust gas in the bags will be higher. This procedure is limited by the water concentration that also increases. Condensation of water in the exhaust bags and in the lines leading therein as well as in the analysis lines, however, must be avoided, since this leads to the falsification of the measurement results (several pollutants are soluble in water and also precipitate therein). This problem is eliminated at the present time by heating the exhaust gas sample bag, sample lines leading thereto from the CVS, as well as the analysis lines.

In heating the sample gas, there is now the problem that in order to avoid condensate, the entire device including the exhaust bag, the sampling lines and the analysis lines must be heated. This extensive heating and temperature regulation plus monitoring are time-consuming and expensive. Since any cold spots in the piping system must be avoided, all valves, for example, must also be at an elevated temperature, which requires an increased expenditure for insulation. The operating costs are also considerable, due to the high consumption of electrical power involved in the heating. In addition, there is no flexibility in the construction of the complete test stand.

SUMMARY OF THE INVENTION

An object of the invention is to provide an apparatus and a process for the analysis of exhaust gas components, which avoid the above-noted disadvantages.

This object is achieved by arranging the sample bag in a gas-tight, pressure resistant container which is maintained under vacuum.

Because the sample bag is arranged in a gas-tight and pressure-resistant container, which is under a vacuum, the vacuum also prevails in the connection lines leading to flow limiters, which are disposed directly at the place of sampling. Due to the reduction in pressure as compared to conventional processes, condensation is avoided in an effective and cost-favorable way.

In order to be able to measure the vacuum in the container, a pressure sensor is assigned to the container. In this way, the vacuum in the container is kept constant during the sampling and thus during the associated filling of the sample bags. A pressure regulator in the vacuum conveyor line is controlled by the pressure sensor to regulate admission of fresh air to maintain the desired vacuum pressure.

In order to avoid unnecessary lines and to make the device as flexible as possible, the pressure sensor, the pressure regulator, valves and also the vacuum conveyor may be arranged directly at the container.

BRIEF DESCRIPTION OF THE DRAWING

The sole FIGURE of the drawing is a diagrammatic illustration of an embodiment of the invention.

DETAILED DESCRIPTION

Referring to the drawing, sample gas is introduced into sample bags 1, 2, 3 from a sampling source (not shown). Particular bags can be selected to receive sample gas by means of valves 4, 5, 6. Valves 7 and 8 serve the purpose of selecting sample flow to valves 4, 5, 6 via flow limiters 9 and 10 in the form of throttles. Bags 1, 2, 3 are connected to an analytical device 14 by means of valves 11, 12 and 13. The sample gas is supplied by a sample-gas pump 15 to the analytical device 14.

According to the invention, sample bags 1, 2 and 3 are arranged in a gas-tight and pressure-resistant container 16. A vacuum is produced in the container 16 and the magnitude of vacuum pressure is detected by a pressure sensor 17 connected by a line to the container or directly mounted on container 16. The pressure sensor 17 can optionally measure the pressure in line in front of a vacuum conveyor 18 as shown by the dotted lines. Container 16 is evacuated by the vacuum conveyor 18 connected by a valve 19 to the container 16. In order to keep the vacuum constant for sample bags 1, 2 and 3 during the filling of the bags, the vacuum conveyor 18 is controlled by pressure sensor 17. The container 16 can be vented by means of valve 20.

The operation is as follows:

Sample bags 1, 2 and 3 are first completely evacuated by closing valves 7 and 8 and opening valves 4, 5, 6 and 19 to connect the bags to vacuum conveyor 18. When the bags are completely evacuated valves 4, 5, 6 and 19 are closed. The vacuum conveyor 18 then evacuates container 16 until a specific vacuum is reached, which is kept constant in the subsequent sampling operation. In order to keep this phase as brief as possible, the container volume should be kept as small as possible.

Bags 1, 2 and 3 are then filled by opening valves 7 and/or 8 as well as valves 4, 5, and 6. The pressure in bags 1, 2 and 3 is always equal to the vacuum pressure in the container 16. Since the vacuum pressure in the container is kept constant by the vacuum conveyor under the control of pressure sensor 17, the volume flow of the sample gas is also always constant, as required for certification. The vacuum prevailing in container 16 also exists in the lines connected to flow limiters 9 and 10, which are introduced appropriately directly at the sampling location. In this way, any water condensation, both in the sample bags as well as in the entire sampling system, is avoided. After concluding the sampling, the sample bags 1, 2 and 3 are again sealed.

For the analysis, sample bags 1, 2 and 3 are connected to the analytical measuring device 14 by opening valves 11, 12 and 13. An analytical conveyor 15 then conveys the sample gas to the analytical device 14. A vacuum also prevails in this line up to analytical conveyor 15.

For flushing the system, all valves are closed. The bags are evacuated by connection to vacuum conveyor 18 via valve 19 and valves 4, 5 and 6. It is also possible to fill sample bags 1, 2 and 3 with a clean gas, for example, nitrogen or synthesized air by means of a valve (not shown) and then to evacuate (flush) them again.

It should be clear that this embodiment is only limited to one particular application. The valves, pressure sensors and the conveyor may also be mounted, for example, directly on container 16. The pressure regulation in the container can also be conducted by conventional pressure regulators. The vacuum conveyor 18 may then have a constant transporting capacity. The bags can also be flushed, for example, by pumping gas into the container by means of a pump and then expelling the gas from the bags. The form of the bag can also be varied. For example, the bags can be of accordion-like shape. The number of bags, the valves assigned thereto, as well as the number of flow limiters are arbitrary. Separate pumps with adapted capacities may also be used for the pressure regulation itself as well as the flushing procedure.

Although the invention is disclosed with reference to particular embodiments thereof, it will become apparent to those skilled in the art that numerous modifications and variations can be made which will fall within the scope and spirit of the invention as defined by the attached claims.

What is claimed is:

1. Apparatus for analyzing exhaust gas components from an internal combustion engine, said apparatus comprising:
    an inlet line for a gas sample,
    at least one sample bag connected for receiving the gas sample,
    an analyzer device connected to receive said gas sample from said at least one sample bag to analyze said gas sample,
    a gas-tight and pressure resistant container containing said at least one sample bag,
    means for evacuating said container to a vacuum pressure,
    a pressure sensor connected to said container to measure pressure in the container, said pressure sensor being connected to said evacuating means to control the vacuum pressure in the container, and
    a plurality of valves controlling connection between said at least one bag, said analyzer device, said pressure sensor and said evacuating means.

2. Apparatus as claimed in claim 1, wherein said valves, said analyzer device, said pressure sensor and said evacuating means are mounted on said container.

3. A process for the analysis of exhaust gas components from an internal combustion engine comprising:
    introducing an exhaust gas sample into a sample bag, in a sampling period,
    conveying the sample gas from the sample bag to an analyzer device during a measurement period,
    subjecting the sample bag to a vacuum during the sampling period by enclosing the sample bag in a gas-tight and pressure resistant container in which said vacuum is maintained,
    connecting the container to a vacuum source and regulating the vacuum in the container by sensing the vacuum in the container and controlling the connection of the vacuum source to the container, the vacuum source being a vacuum conveyor having constant flow, and
    selectively introducing fresh air into said vacuum conveyor in an amount to regulate the vacuum in the container.

* * * * *

UNITED STATES PATENT AND TRADEMARK OFFICE
CERTIFICATE OF CORRECTION

PATENT NO. : 6,282,944 B1
DATED : September 4, 2001
INVENTOR(S) : Torsten Bornemann It is certified that error appears in the above-identified patent and that said Letters Patent is hereby corrected as shown below:

Title page,
Item [30], "995" should read -- 955 --.

Signed and Sealed this

Twelfth Day of March, 2002

Attest:

JAMES E. ROGAN
Director of the United States Patent and Trademark Office

*Attesting Officer*